(12) United States Patent
Jaracz

(10) Patent No.: US 11,234,913 B2
(45) Date of Patent: Feb. 1, 2022

(54) PREPARATION OF ZINC CITRATE AND OF ZINC CITRATE-CONTAINING ORAL CARE COMPOSITIONS

(71) Applicant: Colgate-Palmolive Company, New York, NY (US)

(72) Inventor: Stanislav Jaracz, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 150 days.

(21) Appl. No.: 15/521,058

(22) PCT Filed: Oct. 24, 2014

(86) PCT No.: PCT/US2014/062086
§ 371 (c)(1),
(2) Date: Apr. 21, 2017

(87) PCT Pub. No.: WO2016/064412
PCT Pub. Date: Apr. 28, 2016

(65) Prior Publication Data
US 2017/0354578 A1    Dec. 14, 2017

(51) Int. Cl.
*A61K 8/27* (2006.01)
*A61Q 11/00* (2006.01)
*A61K 8/365* (2006.01)

(52) U.S. Cl.
CPC ........... *A61K 8/365* (2013.01); *A61K 8/27* (2013.01); *A61Q 11/00* (2013.01); *A61K 2800/80* (2013.01); *A61K 2800/805* (2013.01)

(58) Field of Classification Search
CPC ...... A61K 8/365; A61K 8/24; A61K 2800/80; A61K 2800/805; A61Q 11/00
See application file for complete search history.

(56) References Cited

U.S. PATENT DOCUMENTS 4,289,754 A    9/1981    Dhabhar et al.

FOREIGN PATENT DOCUMENTS

| CN | 101935274 A | 1/2011 |
|---|---|---|
| CN | 102329227 A | 1/2012 |
| CN | 102491893 A | 6/2012 |
| EP | 1837009 | 5/2009 |
| GB | 1373002 | 11/1974 |
| GN | 103189040 | 5/2017 |
| WO | WO 1994/014406 | 7/1994 |
| WO | WO 2006/012967 | 2/2006 |

OTHER PUBLICATIONS

He et al., 2011, "Producing zinc citrate, by weighing citric acid, preparing zinc oxide into suspension using distilled water, adding suspension to citric acid solution and extracting and collecting decomposed crystal," Database WPI AN: 2011-B62041.
International Search Report and Written Opinion in International Application No. PCT/US2014/062086, dated Jun. 23, 2015.
CN103189040, Colgate-Palmolive Company, "Oral care product and methods of use and manufacture thereof," Jul. 3, 2013, English language machine translation of abstract, Espacenet, date obtained: Sep. 16, 2019, 1 page <https://worldwide.espacenet.com/publicationDetails/biblio?CC=CN&NR=103189040A&KC=A&FT=D&ND=4&date=20130703&DB=&locale=en EP>.

*Primary Examiner* — Adam C Milligan

(57) ABSTRACT

A method of preparing a zinc citrate-containing oral care composition, the method comprising: (a) adding zinc oxide to a solution of citric acid in a solvent to form a suspension; (b) agitating the suspension until a clear solution is obtained; and (c) adding an additional oral care ingredient to the solution obtained in (b). Also, a method of preparing a zinc citrate-containing oral care composition, the method comprising: (a) adding citric acid to a suspension of zinc oxide in a solvent; (b) agitating the suspension until a clear solution is obtained; and (c) adding an additional oral care ingredient to the solution obtained in (b). In both methods, steps (a) and (b) are carried out at a temperature of from 10° C. to 50° C. and the molar ratio of zinc oxide to citric acid in step (a) is about 3:2.

13 Claims, 1 Drawing Sheet

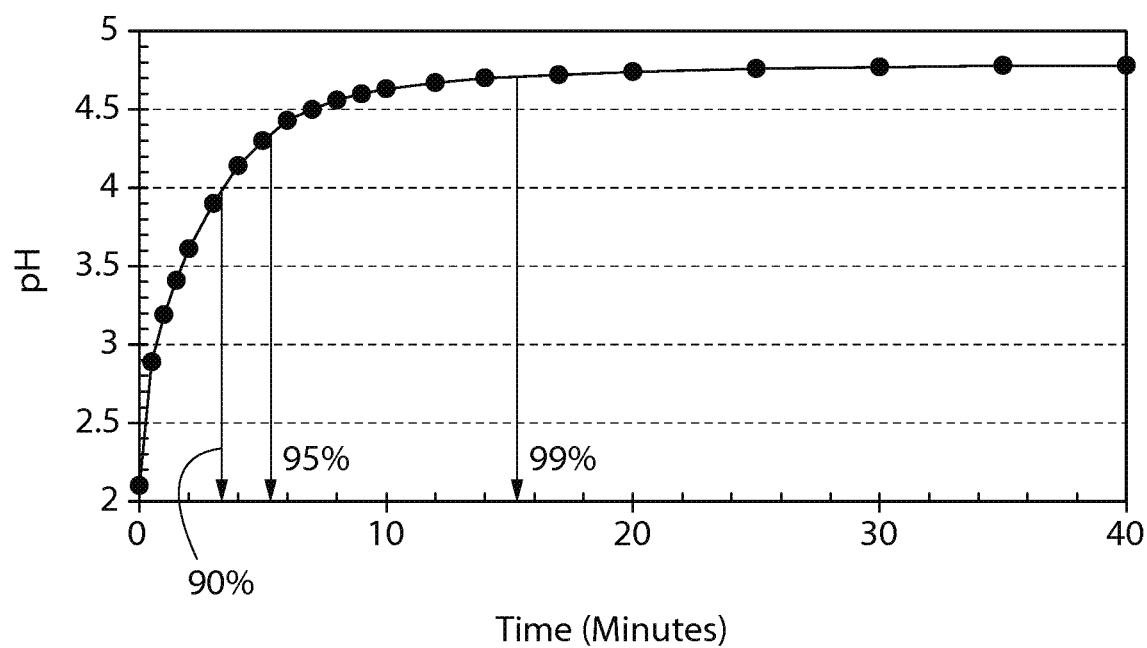

PREPARATION OF ZINC CITRATE AND OF ZINC CITRATE-CONTAINING ORAL CARE COMPOSITIONS

CROSS-REFERENCE TO RELATED APPLICATIONS

This application is a U.S. National Stage Application under 35 U.S.C. § 371 of International Application No. PCT/US2014/062086, filed on Oct. 24, 2014.

BACKGROUND

Zinc salts such as zinc citrate, $[Zn_3(citrate)_2]$, may be included in oral care compositions to provide various benefits. However, commercially-available zinc citrate has been found to be poorly soluble in water, and its solubility can also vary from batch to batch. It has also been observed that the concentration of solubilized zinc citrate in oral care compositions containing zinc citrate can vary over time. Zinc citrate is also a relatively expensive material as compared to other zinc salts and to citric acid. It would therefore be desirable to provide zinc citrate-containing oral care compositions in which the concentration of solubilized zinc citrate is increased, in which the concentration of solubilized zinc citrate is consistent over time, and which also represent a cost saving with regard to the zinc citrate included therein.

BRIEF SUMMARY

In a first aspect, the present invention provides a method of preparing a zinc citrate-containing oral care composition, the method comprising:
 (a) adding zinc oxide to a solution of citric acid in a solvent to form a suspension;
 (b) agitating the suspension until a clear solution is obtained; and
 (c) adding an additional oral care ingredient to the solution obtained in (b);
wherein steps (a) and (b) are carried out at a temperature of from 10° C. to 50° C. and wherein the molar ratio of zinc oxide to citric acid in step (a) is about 3:2.

Optionally, steps (a) and (b) are carried out at a temperature of from 15° C. to 35° C. Further optionally, steps (a) and (b) are carried out at a temperature of from 20° C. to 25° C.

Optionally, steps (a) and (b) are carried out at a temperature of from 25° C. to 35° C. Further optionally, steps (a) and (b) are carried out at a temperature of from 30° C. to 35° C.

Optionally, the solvent is water.

Optionally, the solvent is a combination of water and sorbitol. Further optionally, the concentration of sorbitol is 50 weight % or less based on the total weight of the solvent.

Optionally, the weight ratio of citric acid to solvent in step (a) is from 1:27 to 1:2500.

Further optionally, the weight ratio of citric acid to solvent in step (a) is from 1:50 to 1:500.

Optionally, the agitating in (b) is carried out for from 1 to 120 minutes, optionally from 3.5 minutes to 60 minutes. Further optionally, the agitating in (b) is carried out for from 5 minutes to 30 minutes, optionally from 5 minutes to 10 minutes.

Optionally, the zinc citrate is formed in situ during the method of preparing the oral care composition.

Optionally, the additional oral care ingredient is an abrasive, a diluent, a bicarbonate salt, a pH modifying agent, a surfactant, a foam modulator, a thickening agent, a humectant, a sweetener, a flavorant, a colorant, an antibacterial agent, an anticaries agent, a saliva-stimulating agent, an antisensitivity agent, an antioxidant, an anticalculus agent, or a combination of any two or more thereof.

Optionally, the oral care composition is a toothpaste, a gel, a mouthwash, a mouthrinse, a spray, or a film.

In a second aspect, the present invention provides a method of preparing a zinc citrate-containing oral care composition, the method comprising:
 (a) adding citric acid to a suspension of zinc oxide in a solvent;
 (b) agitating the suspension until a clear solution is obtained; and
 (c) adding an additional oral care ingredient to the solution obtained in (b);
wherein steps (a) and (b) are carried out at a temperature of from 10° C. to 50° C. and wherein the molar ratio of zinc oxide to citric acid in step (a) is about 3:2.

Optionally, steps (a) and (b) are carried out at a temperature of from 15° C. to 35° C. Further optionally, steps (a) and (b) are carried out at a temperature of from 20° C. to 25° C.

Optionally, steps (a) and (b) are carried out at a temperature of from 25° C. to 35° C. Further optionally, steps (a) and (b) are carried out at a temperature of from 30° C. to 35° C.

Optionally, the solvent is water.

Optionally, the solvent is a combination of water and sorbitol. Further optionally, the concentration of sorbitol is 50 weight % or less based on the total weight of the solvent.

Optionally, the weight ratio of citric acid to solvent in step (a) is from 1:27 to 1:2500. Further optionally, the weight ratio of citric acid to solvent in step (a) is from 1:50 to 1:500.

Optionally, the agitating in (b) is carried out for from 1 to 120 minutes, optionally from 3.5 minutes to 60 minutes. Further optionally, the agitating in (b) is carried out for from 5 minutes to 30 minutes, optionally from 5 minutes to 10 minutes.

Optionally, the zinc citrate is formed in situ during the method of preparing the oral care composition.

Optionally, the additional oral care ingredient is an abrasive, a diluent, a bicarbonate salt, a pH modifying agent, a surfactant, a foam modulator, a thickening agent, a humectant, a sweetener, a flavorant, a colorant, an antibacterial agent, an anticaries agent, a saliva-stimulating agent, an antisensitivity agent, an antioxidant, an anticalculus agent, or a combination of any two or more thereof.

Optionally, the oral care composition is a toothpaste, a gel, a mouthwash, a mouthrinse, a spray, or a film.

In a fourth aspect, the present invention provides a method of increasing the uptake of zinc ions from an oral care composition, comprising preparing the oral care composition by a method according to the present invention.

Optionally, the uptake of zinc ions is uptake of zinc ions by skin.

Optionally, the uptake of zinc ions is uptake of zinc ions by soft tissue of an oral cavity.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

FIG. 1 shows the pH of the reaction mixture when zinc oxide is added to a solution of citric acid in water, as monitored during the course of the reaction.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

All ratios expressed herein should be understood to refer to ratios by weight, unless otherwise specified.

In a first aspect, the present invention provides a method of preparing a zinc citrate-containing oral care composition, the method comprising:

(a) adding zinc oxide to a solution of citric acid in a solvent to form a suspension;

(b) agitating the suspension until a clear solution is obtained; and (c) adding an additional oral care ingredient to the solution obtained in (b);

wherein steps (a) and (b) are carried out at a temperature of from 10° C. to 50° C. and wherein the molar ratio of zinc oxide to citric acid in step (a) is about 3:2.

In a second aspect, the present invention provides a method of preparing a zinc citrate-containing oral care composition, the method comprising:

(a) adding citric acid to a suspension of zinc oxide in a solvent;

(b) agitating the suspension until a clear solution is obtained; and (c) adding an additional oral care ingredient to the solution obtained in (b);

wherein steps (a) and (b) are carried out at a temperature of from 10° C. to 50° C. and wherein the molar ratio of zinc oxide to citric acid in step (a) is about 3:2.

Zinc oxide is insoluble in water, and forms a suspension on addition thereto. The state of completion of the reaction between zinc oxide and citric acid in steps (a) and (b) to form zinc citrate can be determined visually, as a clear solution is obtained when all of the zinc oxide has reacted with the citric acid to form the solution of zinc citrate.

The present inventors have surprisingly found that solutions which are prepared in accordance with steps (a) and (b) of the above methods have higher concentrations of solubilized zinc citrate than solutions which are prepared by addition of commercially-available zinc citrate to a solvent. This increase in the concentration of solubilized zinc citrate results in greater bioavailability of zinc ions in those solutions which are prepared in accordance with steps (a) and (b) of the above methods, as compared to solutions prepared by adding commercially-available zinc citrate to a solvent. Zinc citrate solutions prepared according to steps (a) and (b) of the above methods also exhibit consistent levels of solubilized zinc citrate upon aging, in contrast to solutions prepared by adding commercially-available zinc citrate to a solvent (which have been shown to exhibit an increase in concentration of solubilized zinc citrate upon aging).

The oral care compositions prepared according to the above methods of the present invention also have higher concentrations of solubilized zinc citrate than compositions prepared by adding commercially-available zinc citrate to a base formulation. This results in greater bioavailability of zinc ions in compositions prepared according to the present invention, as compared to compositions prepared by adding commercially-available zinc citrate to a base formulation. Oral care compositions prepared in accordance with the present invention also exhibit consistent levels of solubilized zinc citrate upon aging, in contrast to compositions prepared by adding commercially-available zinc citrate to a base formulation (which show an increase in concentration of solubilized zinc citrate upon aging), thus improving product quality control. The levels of solubilized zinc citrate would also be consistent from batch to batch of an oral care composition produced by the method of the present invention (in contrast to a composition prepared by adding commercially-available zinc citrate to a base formulation, as the solubility of such zinc citrate can vary between batches thereof), thus further improving quality control.

In some embodiments, steps (a) and (b) are carried out at a temperature of from 15° C. to 50° C., from 15° C. to 45° C., from 15° C. to 40° C., from 15° C. to 35° C., from 15° C. to 32° C., from 20° C. to 30° C., from 20° C. to 25° C., from 20° C. to 23.5° C., or about 22° C.

In some embodiments, steps (a) and (b) are carried out at a temperature of from 25° C. to 35° C. or from 30° C. to 35° C.

In some embodiments, the weight ratio of solvent to citric acid in step (a) is at least 27:1, or at least 50:1. In some embodiments, the weight ratio of citric acid to solvent in step (a) is from 1:27 to 1:2500, from 1:50 to 1:2500, from 1:50 to 1:1650, from 1:50 to 1:500, from 1:50 to 1:330, from 1:50 to 1:250, from 1:50 to 1:165, or from 1:50 to 1:66. In some embodiments, the weight ratio of citric acid to solvent in step (a) is from 1:150 to 1:1650, or from 1:330 to 1:1650.

In some embodiments, the weight ratio of citric acid to solvent in step (a) is about 1:2500, about 1:1650, about 1:330, about 1:165, or about 1:66.

In some embodiments, the solvent is water.

In some embodiments, the solvent is a combination of water and sorbitol. In certain such embodiments, the concentration of sorbitol is 50 weight % or less based on the total weight of the solvent. In certain embodiments, the concentration of sorbitol is from 5 to 50 weight % based on the total weight of the solvent.

In some embodiments, the agitating in (b) is carried out for from 1 minute to 120 minutes, from 3 minutes to 90 minutes, from 3.5 minutes to 60 minutes, from 5 minutes to 60 minutes, from 5 minutes to 45 minutes, from 5 minutes to 30 minutes, from 5 minutes to 20 minutes, from 5 minutes to 16 minutes, or from 5 minutes to 10 minutes. In some embodiments, the agitating in step (b) is carried out for from 3 minutes to 20 minutes, from 3.5 minutes to 15.5 minutes, from 5.5 minutes to 15.5 minutes, or for about 3.5 minutes, about 5.5 minutes, or about 15.5 minutes.

In some embodiments, the zinc citrate is formed in situ during the method of preparing the oral care composition.

In some embodiments, the oral care composition is a toothpaste, a gel, a mouthwash, a mouthrinse, a spray, or a film (which may be wholly or partially dissolvable, or indissolvable). In some embodiments, the oral care composition is a mouthwash. In some embodiments, the oral care composition is a toothpaste.

In some embodiments, the additional oral care ingredient is an abrasive, a diluent, a bicarbonate salt, a pH modifying agent, a surfactant, a foam modulator, a thickening agent, a humectant, a sweetener, a flavorant, a colorant, an antibacterial agent, a saliva-stimulating agent, an antisensitivity agent, an antioxidant, an anticaries agent, an anticalculus agent, or a combination of any two or more thereof.

In some embodiments, the additional oral care ingredient comprises at least one bicarbonate salt useful for example to impart a "clean feel" to teeth and gums due to effervescence and release of carbon dioxide. Any orally acceptable bicarbonate can be used. The one or more additional bicarbonate salts are optionally present in a total amount of 0.1 weight % to 50 weight %, for example 1 weight % to 20 weight %, by total weight of the composition.

The additional oral care ingredient may also comprise at least one surfactant. Any orally acceptable surfactant, most of which are anionic, nonionic or amphoteric, can be used. One or more surfactants are optionally present in a total amount of 0.01 weight % to 10 weight %, for example, from 0.05 weight % to 5 weight %, or from 0.1 weight % to 2 weight % by total weight of the composition.

The additional oral care ingredient may also comprise at least one humectant, optionally in an amount of from 5 weight % to 60 weight %, from 10 weight % to 50 weight %, from 10 weight % to 40 weight %, or from 15 weight % to 30 weight % by total weight of the composition. Examples of suitable humectants include glycerin and sorbitol.

The additional oral care ingredient may also comprise at least one thickening agent, optionally in an amount of from 0.1 to 20 weight % by total weight of the composition. Examples of thickening agents include thickening silicas and thickening gums (e.g. xanthan gum, cellulose gums).

The additional oral care ingredient may comprise at least one foam modulator, useful for example to increase amount, thickness or stability of foam generated by the composition upon agitation. Any orally acceptable foam modulator can be used, optionally in a total amount of 0.1 weight % to 10 weight %, for example from 0.2 weight % to 5 weight %, or from 0.25 weight % to 2 weight %, by total weight of the composition.

The additional oral care ingredient may comprise at least one sweetener (such as, for example, sodium saccharin), useful for example to enhance taste of the composition. One or more sweeteners are optionally present in a total amount depending strongly on the particular sweetener(s) selected, but typically 0.005 weight % to 5 weight %, by total weight of the composition, optionally 0.005 weight % to 0.2 weight %, further optionally 0.05 weight % to 0.1 weight % by total weight of the composition.

The additional oral care ingredient may also comprise at least one flavorant, useful for example to enhance taste of the composition. One or more flavorants are optionally present in a total amount of from 0.01 weight % to 5 weight %, for example, from 0.03 weight % to 2.5 weight %, optionally 0.05 weight % to 1.5 weight %, further optionally 0.1 weight % to 0.3 weight % by total weight of the composition.

The additional oral care ingredient may comprise at least one colorant. Colorants herein include pigments, dyes, lakes and agents imparting a particular luster or reflectivity such as pearling agents. Any orally acceptable colorant can be used. One or more colorants are optionally present in a total amount of from 0.001 weight % to 20 weight %, for example, from 0.01 weight % to 10 weight %, or from 0.1 weight % to 5 weight %, by total weight of the composition.

The additional oral care ingredient may also comprise an anticaries agent, for example a fluoride ion source. In certain embodiments, the oral care composition of the invention may also contain a source of fluoride ions or fluorine-providing ingredient in amounts sufficient to supply 50 to 5000 ppm fluoride ion, e.g., from 100 to 1000, from 200 to 500, or about 250 ppm fluoride ion. Fluoride ion sources may be added to the compositions of the invention at a level of 0.001 weight % to 10 weight %, e.g., from 0.003 weight % to 5 weight %, 0.01 weight % to 2 weight %, 0.01 weight % to 1 weight %, or about 0.05 weight %. However, it is to be understood that the weights of fluoride salts to provide the appropriate level of fluoride ion will obviously vary based on the weight of the counter ion in the salt, and one of skill in the art may readily determine such amounts. A preferred fluoride salt may be sodium fluoride.

The additional oral care ingredient may comprise a saliva stimulating agent useful, for example, in amelioration of dry mouth. Any orally acceptable saliva stimulating agent can be used. One or more saliva stimulating agents are optionally present in saliva stimulating effective total amount.

The additional oral care ingredient may include antisensitivity agents. Such agents may be added in effective amounts, e.g., from 1 weight % to 20 weight % by weight based on the total weight of the composition, depending on the agent chosen.

The additional oral care ingredient may further comprise an antioxidant. Any orally acceptable antioxidant can be used.

The additional oral care ingredient may comprise a tartar control (anticalculus) agent, for example in an amount of from 1 to 5 weight %, or from 2 to 3 weight %. An example of a tartar control agent is tetrasodium pyrophosphate.

EXAMPLES

Example 1

0.389 kg Zinc oxide was added to a solution of 0.612 kg citric acid in 17 litres of water. The resulting suspension was then agitated by stirring at room temperature (22° C.) for 30 minutes. A clear solution of zinc citrate was obtained. It was noted that most of the reaction was completed after 5 minutes of agitation. The amount of zinc citrate formed by completion of the above reaction (molar ratio of zinc oxide: citric acid of 3:2) was calculated to be 0.914 kg (equivalent to 1 kg zinc citrate trihydrate).

It is noted that, at the time of performing the above reaction, the price of 1 kg commercially-available zinc citrate trihydrate was US$7.62, whereas the price of the above amounts of zinc oxide and citric acid was US$2.72 and US$2.03, respectively. The total price of the ingredients used in the method of the present invention is US$4.75, which represents a cost saving of 38% as compared to the price of the equivalent amount of commercially-available zinc citrate.

Example 2

The solubility of commercially-available zinc citrate was then evaluated.

In a process according to the present invention, zinc oxide was added to a solution of citric acid in water, and the resulting suspension was agitated for 30 minutes to obtain a clear solution (the "Example" solution). The amounts of zinc oxide, citric acid and water were chosen so as to result in production of a solution of 2.4 weight % zinc citrate.

0.24 g commercially-available zinc citrate was added to 9.76 g water, to form a "Comparative" solution of 2.4 weight % zinc citrate (if all of the zinc citrate were to dissolve in the solvent).

The concentration of solubilized zinc citrate in the Comparative solution was determined at various time points after its formation. The results are shown in Table 2:

TABLE 2

| Time after Comparative solution formation | Concentration of solubilized zinc citrate (weight %) |
| --- | --- |
| 0 days (1 hr after formation) | 0.255 |
| 1 day | 0.306 |
| 2 days | 0.317 |
| 13 days | 0.319 |

The "Example" solution gave a solubilized zinc citrate concentration of 2.4 weight % 30 minutes after its preparation, and no crystallization of zinc citrate from this solution was observed even after aging for one week, indicating that there was no change in the solubilized zinc citrate concentration and it remained at the 2.4 weight % level.

A second "Example" solution was prepared by the method according to the invention (as detailed for the 2.4 weight % zinc citrate "Example" solution, above), with the amounts of zinc oxide, citric acid and water chosen so as to result in production of a solution of 6 weight % zinc citrate (i.e. 0.233 g zinc oxide and 0.367 g citric acid in 9.40 g water). The preparation was carried out at 35° C. This solution also showed no signs of crystallization of zinc citrate after aging for 30 minutes after preparation, indicating that there was no change in the solubilized zinc citrate concentration.

Example 3

A 1.26 weight % solution of zinc citrate as prepared by the method of the present invention as set out for the "Example" solution in Example 2 above, and a 1.26 weight % zinc citrate solution obtained by dissolving commercially available zinc citrate in water, were tested for uptake to Vitro-Skin. Vitro-Skin® is a testing substrate (available from IMS Technologies) that effectively mimics the surface properties of human skin. It contains both optimized protein and lipid components and is designed to have topography, pH, critical surface tension and ionic strength similar to human skin.

The protocol for the uptake assay is as follows:
1. Cut Vitro-skin (IMS Inc., Portland, Me.) into uniform circles of diameter between 10 to 14 mm. Cork borer may be used. The exact diameter is necessary to calculate uptake per square centimeter.
2. Rinse the Vitro-skin circles (in bulk) briefly 3 times with hexanes. Air dry to evaporate hexanes.
3. Soak Vitro-skin in sterilized and cleared saliva overnight in disposable polystyrene Falcon tube. Use 1 mL of saliva per tissue. Perform in triplicate.
4. Aspirate saliva, add 1 mL of the studied solution and incubate for 2 minutes in 37° C. water bath.
5. Aspirate the solution and rinse 3-times with 5 mL of deionized water for 10 seconds each. Use vortex for rinsing (max speed). Transfer the tissue into new polystyrene Falcon tube.
6. Digest the Vitro-Skin tissue in 1 mL concentrated nitric acid until it dissolves, then dilute with deionized water to 10 mL and measure concentration of zinc using atomic spectroscopy.
7. The obtained level of zinc ions (typically in µg/mL) equals numerically to the µg per tissue (UT).
8. To calculate uptake of zinc ions per square centimeter, use the following formula:

$$UR = 2 \ast UT/(\pi \ast d2)[\mu g/cm^2]$$

where:
UR is (relative) uptake of zinc ions per square centimeter of Vitro-skin (both sides)
UT is uptake of zinc ions per tissue
$\pi$ is 3.14159 . . .
d is diameter of the tissue in centimeters.

Data for the average uptake of zinc ions in the Vitro-Skin® assay for the two zinc citrate solutions are set forth in Table 3 (below):

TABLE 3

| | Uptake (µg Zn/cm²) |
| --- | --- |
| Zinc citrate solution prepared according to method of present invention | 50.40 |
| Zinc citrate solution prepared by dissolving commercially available zinc citrate in water | 38.09 |

As can be seen from Table 3, above, greater uptake of zinc ions was observed from the solution prepared according to the present invention, as opposed to the solution prepared by dissolving commercially-available zinc citrate in water.

Example 4

The pH of the suspension formed by adding zinc oxide to a solution of citric acid in water was monitored during the course of the reaction, in order to assess the completion of the reaction between the zinc oxide and citric acid (in a molar ratio of 3:2) to form zinc citrate. The pH was shown to increase during the course of the reaction, with a levelling-out of the pH observed when the reaction had reached its end-point i.e. when all of the zinc oxide and citric acid had reacted to form zinc citrate.

In a First Procedure, 612 mg citric acid was dissolved in 17 g water in a scintillation vial. The initial pH of the solution was measured (i.e. at time t=0 min). 389 mg zinc oxide (corresponding to a molar ratio of zinc oxide to citric acid of 3:2) was then added with stirring, and the pH of the stirred reaction mixture was monitored for 3 hours. The reaction was carried out at a temperature of 22° C.

The results of the pH monitoring are shown in Table 4, below, and also in FIG. 1:

TABLE 4

| Time/min | pH | Appearance |
| --- | --- | --- |
| 0.0 | 2.10 | |
| 0.5 | 2.89 | |
| 1.0 | 3.19 | |
| 1.5 | 3.41 | |
| 2.0 | 3.61 | |
| 3.0 | 3.90 | |
| 4.0 | 4.14 | |
| 5.0 | 4.30 | |
| 6.0 | 4.43 | |
| 7.0 | 4.50 | |
| 8.0 | 4.56 | |
| 9.0 | 4.60 | opaque |
| 10.0 | 4.63 | |
| 12.0 | 4.67 | |
| 14.0 | 4.70 | |
| 17.0 | 4.72 | |
| 20.0 | 4.74 | |
| 25.0 | 4.76 | near clear |
| 30.0 | 4.77 | clear |
| 35.0 | 4.78 | |
| 40.0 | 4.78 | |
| ~3 h | 4.81 | |

In order to determine the time at which the reaction had reached 90%, 95% and 99% completion (as it was not possible to determine this from the results obtained in Table 4 alone), a Second Procedure was carried out. In this procedure, the pH of the First Procedure reaction mixture at 90%, 95% and 99% completion was determined.

A solution of 612 mg citric acid in 17 g water was made up. 350.3 g zinc oxide was then added (which corresponds to 90% of the total amount of zinc oxide needed for a 3:2 ratio of zinc oxide to citric acid), and the reaction allowed to stir for 1 hr, at which time the pH of the reaction mixture was measured ("measurement #1"). A further 19.4 mg zinc oxide was then added (i.e. the total amount of zinc oxide added to the mixture corresponds to 95% of the total amount of zinc oxide needed for a 3:2 ratio of zinc oxide to citric acid), and the reaction allowed to stir for a further hour, at which time the pH of the reaction mixture was measured ("measurement #2"). A further 15.5 mg zinc oxide was then added (i.e. the total amount of zinc oxide added to the mixture corresponds to 99% of the total amount of zinc oxide needed for a 3:2 ratio of zinc oxide to citric acid), and the reaction allowed to stir for a further hour, at which time the pH of the reaction mixture was measured ("measurement #3"). The results are shown in Table 5, below. In these results, the pH at Measurement #1 corresponds to the pH of the reaction mixture in the First Procedure at 90% completion; the pH at Measurement #2 corresponds to the pH of the reaction mixture in the First Procedure at 95% completion; and the pH at Measurement #3 corresponds to the pH of the reaction mixture in the First Procedure at 99% completion.

TABLE 5

| Measurement # | % of the total amount of ZnO needed for a 3:2 ratio of ZnO:citric acid | pH |
|---|---|---|
| 1 | 90% | 4.02 |
| 2 | 95% | 4.36 |
| 3 | 99% | 4.71 |

As can be seen from Table 5, the pH corresponding to 90% completion was 4.02; the pH corresponding to 95% completion was 4.36; and the pH corresponding to 99% completion was 4.71.

In order to determine the time at which the reaction in the First Procedure had reached 90%, 95% and 99% completion, the results in Table 4 were plotted on a graph (as shown in FIG. 1) and the times at which the pH reached the above values of 4.02 (corresponding to 90% completion), 4.36 (corresponding to 95% completion) and 4.71 (corresponding to 99% completion) were determined from this graph. As shown in FIG. 1, the reaction was 90% complete at 3.5 minutes; 95% complete at 5.5 minutes, and 99% complete at 15.5 minutes. Thus a zinc citrate solution of high purity and high zinc citrate concentration can be obtained within a short period of time by the methods of the present invention.

Example 5

An example of an oral care composition which may be formed by the methods of the present invention is shown in Table 6, below.

TABLE 6

| Ingredient | Amount (weight %) |
|---|---|
| Zinc citrate | 0.1-10 |
| Surfactants | 0.1-2 |
| Humectants | 10-40 |
| Anticaries agents | 0.01-2 |
| Thickening agents | 0.1-20 |
| Anticalculus agents | 2-3 |
| Water & minors (colorants, flavorants, sweeteners etc.) | QS |

What is claimed is:

1. A method of preparing a zinc citrate-containing oral care composition, the method comprising:
    (a) adding zinc oxide to a solution of citric acid in water to form a suspension;
    (b) agitating the product of step (a) for 1 to 120 minutes until a clear solution is obtained; and
    (c) adding an additional oral care ingredient to the solution obtained in step (b);
    wherein steps (a) and (b) are carried out at a temperature of from 15° C. to 35° C.;
    wherein the molar ratio of zinc oxide to citric acid in step (a) is 3:2; and
    wherein the solution obtained in step (b) has a pH between 4 and 4.81.

2. A method of preparing a zinc citrate-containing oral care composition, the method comprising:
    (a) adding citric acid to a suspension of zinc oxide in water;
    (b) agitating the product of step (a) for 1 to 120 minutes until a clear solution is obtained; and
    (c) adding an additional oral care ingredient to the solution obtained in step (b);
    wherein steps (a) and (b) are carried out at a temperature of from 15° C. to 35° C.,
    wherein the molar ratio of zinc oxide to citric acid in step (a) is 3:2; and
    wherein the solution obtained in step (b) has a pH between 4 and 4.81.

3. The method of claim 1, wherein steps (a) and (b) are carried out at a temperature of from 20° C. to 25° C.

4. The method of claim 1, wherein steps (a) and (b) are carried out at a temperature of from 25° C. to 35° C.

5. The method of claim 4, wherein steps (a) and (b) are carried out at a temperature of from 30° C. to 35° C.

6. The method of claim 1, wherein the weight ratio of citric acid to water in step (a) is from 1:27 to 1:2500.

7. The method of claim 6, wherein the weight ratio of citric acid to water in step (a) is from 1:50 to 1:500.

8. The method of claim 1, wherein the agitating in (b) is carried out for from 5 minutes to 30 minutes.

9. The method of claim 1, wherein the additional oral care ingredient is an abrasive, a diluent, a bicarbonate salt, a pH modifying agent, a surfactant, a foam modulator, a thickening agent, a humectant, a sweetener, a flavorant, a colorant, an antibacterial agent, a saliva-stimulating agent, an antisensitivity agent, an antioxidant, an anticaries agent, an anticalculus agent, or a combination of any two or more thereof.

10. The method of claim 1, wherein the method is substantially free from the addition of alkali hydroxide and/or ammonium hydroxide bases.

11. The method of claim 10, wherein the method is substantially free from the addition of sodium hydroxide and/or ammonium hydroxide.

12. The method of claim 1, wherein the zinc citrate is formed in situ during the method of preparing the oral care composition.

13. The method of claim 1, wherein the oral care composition is a toothpaste, a gel, a mouthwash, a mouthrinse, a spray, or a film.

\* \* \* \* \*